US007824228B1

(12) United States Patent
Yang et al.

(10) Patent No.: US 7,824,228 B1
(45) Date of Patent: Nov. 2, 2010

(54) AUDIO PLUG CONNECTOR

(75) Inventors: Chih-Lin Yang, Taipei Hsien (TW); Hsin-Tsung Ho, Taipei Hsien (TW)

(73) Assignee: Cheng Uei Precision Industry Co., Ltd., Taipei (TW)

( * ) Notice: Subject to any disclaimer, the term of this patent is extended or adjusted under 35 U.S.C. 154(b) by 0 days.

(21) Appl. No.: 12/542,712

(22) Filed: Aug. 18, 2009

(51) Int. Cl.
*H01R 24/04* (2006.01)
*A61N 1/375* (2006.01)

(52) U.S. Cl. ..................................................... 439/668

(58) Field of Classification Search ................. 439/668, 439/669
See application file for complete search history.

(56) References Cited

U.S. PATENT DOCUMENTS

| | | | | |
|---|---|---|---|---|
| 6,461,198 | B1 * | 10/2002 | Chao | 439/668 |
| 6,616,487 | B1 * | 9/2003 | Lai | 439/668 |
| 6,659,805 | B2 * | 12/2003 | Siddiqui et al. | 439/668 |
| 6,964,586 | B2 * | 11/2005 | Siddiqui | 439/669 |
| 6,991,497 | B1 * | 1/2006 | Lin | 439/668 |
| D529,868 | S * | 10/2006 | Shimizu | D13/147 |
| D550,159 | S * | 9/2007 | Kawanobe | D13/146 |
| 7,553,195 | B2 * | 6/2009 | Matsumoto et al. | 439/669 |
| 2006/0009082 | A1 * | 1/2006 | Lin | 439/668 |

* cited by examiner

*Primary Examiner*—James Harvey

(57) ABSTRACT

An audio plug connector for mating with an audio jack connector includes a main member of cylindrical shape with a plurality of contacts exposed along an axis direction thereof. A subsidiary member is extended from a portion of an outer peripheral surface of the main member and defines at least one terminal groove at a lateral surface thereof. A front end of a bottom of the terminal groove is concaved downwards and passes through a lower portion of a front wall of the terminal groove to form a fixing groove, with a stopping portion traversing above the fixing groove. At least one conductive terminal receives in the terminal groove with a rear end thereof extended beyond a rear end of the terminal groove. A front end of the conductive terminal extends oppositely to form a buckling portion inserted into the fixing groove and restrained beneath the stopping portion.

6 Claims, 3 Drawing Sheets

AUDIO PLUG CONNECTOR

BACKGROUND OF THE INVENTION

1. Field of the Invention

The present invention relates to an electrical connector, and more particularly to an audio plug connector capable of transmitting audio signals.

2. The Related Art

Plug-and-jack type connectors are widely used for connecting audio equipments. The plug-and-jack type connectors only transmit audio signals in an earlier stage due to limitations in their structures. Later on, a number of independent terminals are provided on the plug connector for transmitting other signals. A conventional audio plug connector includes an insulating housing which retains an audio plug and also has a plurality of terminal grooves for correspondingly receiving a plurality of independent terminals therein. The terminal has a substantially strip shaped contacting portion for being electrically connected with a mated terminal of a mated audio jack connector.

While the audio plug connector is electrically connected with the mated audio jack connector, a free end of contacting portion of the terminal would likely be tilted out of the terminal groove due to an interference occurred between the terminal and the mated terminal of the audio jack connector. Besides, the terminals have a tendency to slide rearward because they are provided with a backward force from the mated terminals during the insertion. As a result, the terminals may be received in the terminal grooves unstably after the audio plug connector is inserted in and pulled out of the audio jack connector several times. These will cause a bad effect to the audio plug connector and sequentially have influence on the signal transmission.

SUMMARY OF THE INVENTION

An object of the present invention is to provide an audio plug connector having an improved terminal firmly fixed thereto. The audio plug connector includes a main member of substantially cylindrical shape with a plurality of contacts exposed along an axis direction thereof and a subsidiary member extended from a portion of an outer peripheral surface of the main member. The subsidiary member defines at least one terminal groove at a lateral surface thereof. The terminal groove extends substantially parallel with the axis direction of the main member to penetrate a rear end which is finally inserted into a mated audio jack connector. A front end of a bottom of the terminal groove is concaved downwards and passes through a lower portion of a front wall of the terminal groove to form a fixing groove, with a stopping portion traversing above the fixing groove. At least one conductive terminal of strip shape is received in the corresponding terminal groove. A rear end of the conductive terminal extends out of a rear end of the terminal groove, while a front end of the conductive terminal is bent and extended opposite to the rear end of the conductive terminal to form a buckling portion inserted into the corresponding fixing groove of the subsidiary member, with a free end thereof restrained beneath the stopping portion.

As described above, because the buckling portion is inserted into the fixing groove and stopped by the stopping portion, the conductive terminal will not be tilted outside or relatively slide in the terminal groove in insertion and withdrawal, which guarantees the audio plug connector to have a stable transmission with a mated audio jack connector.

BRIEF DESCRIPTION OF THE DRAWINGS

The present invention will be apparent to those skilled in the art by reading the following description of an embodiment thereof, with reference to the attached drawings, in which.

DETAILED DESCRIPTION OF THE PREFERRED EMBODIMENT

Figure 1:
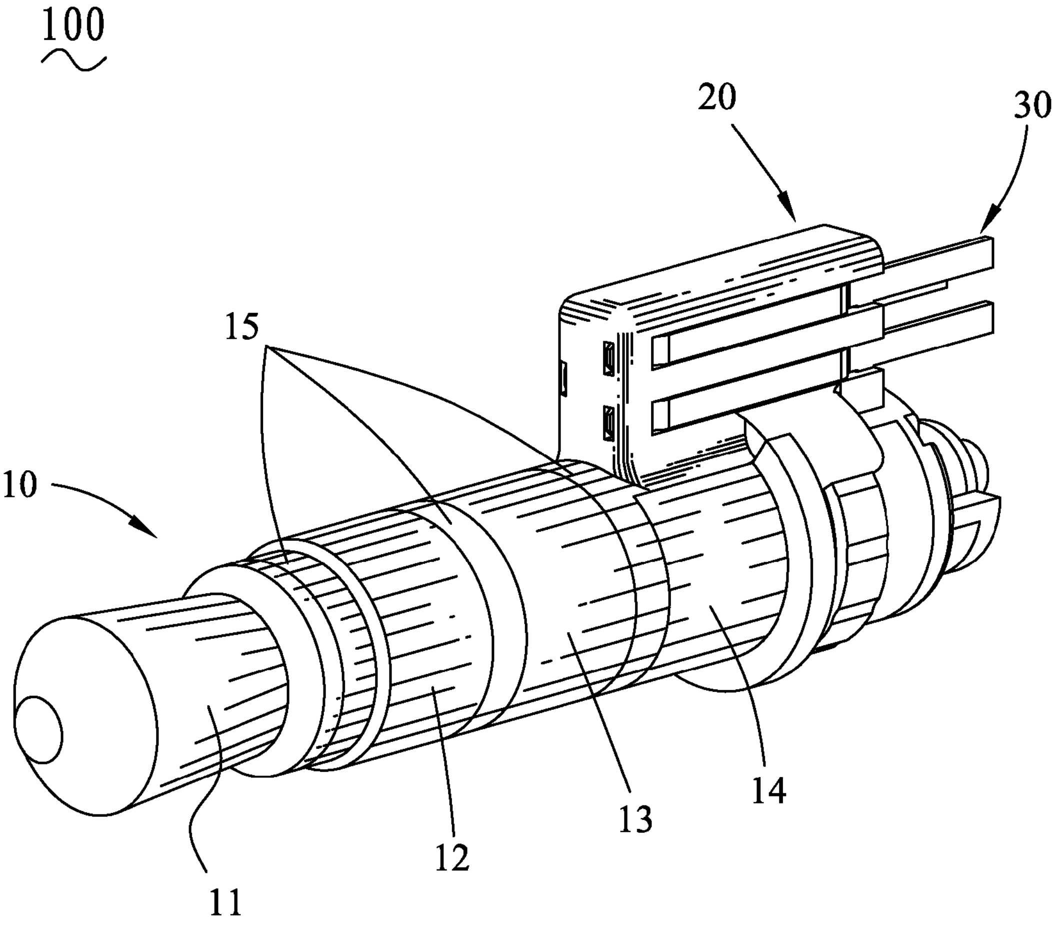
FIG. 1 is a perspective view of an audio plug connector in accordance with the present invention.
Figure 2:
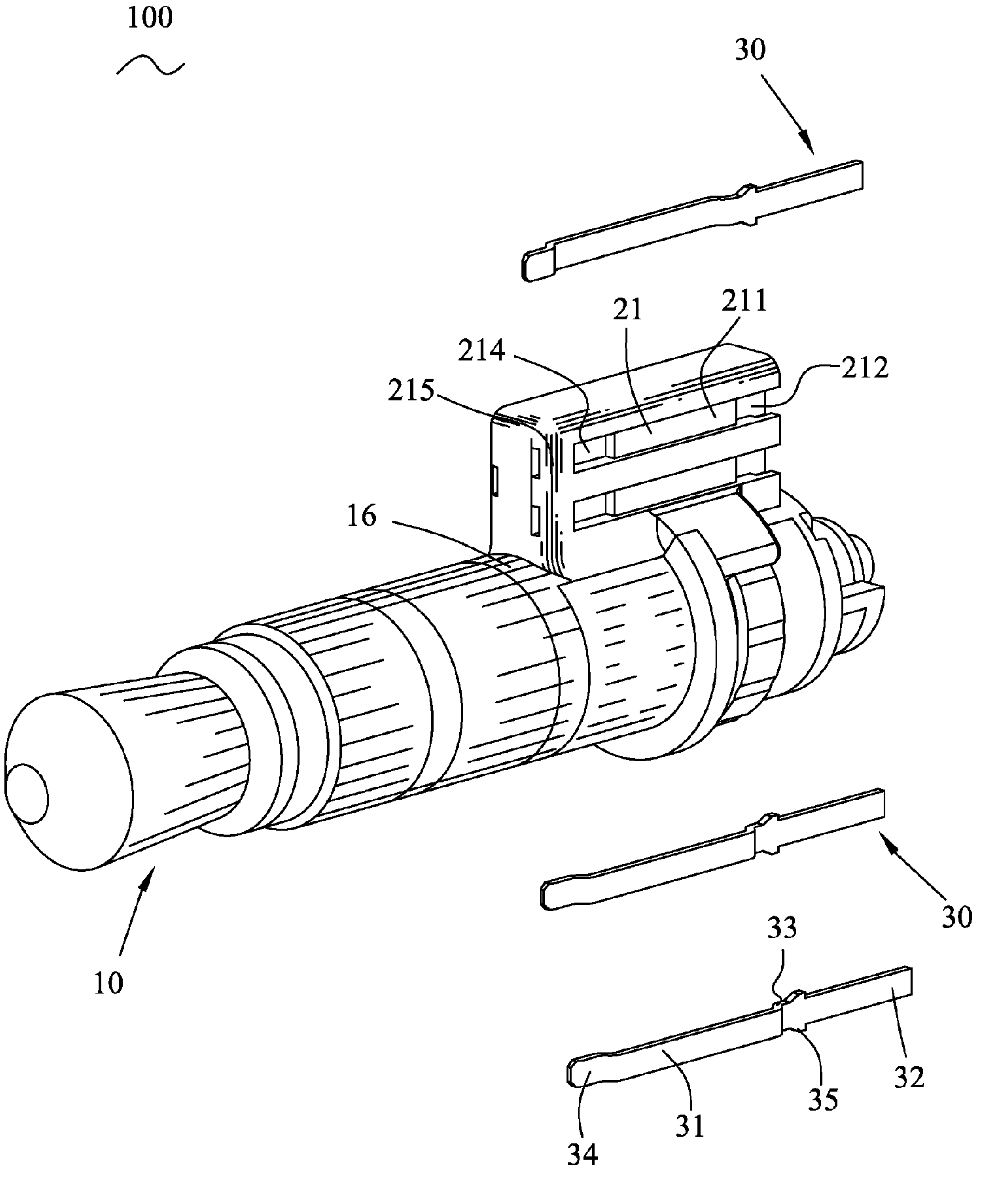
FIG. 2 is a partially exploded view of the audio plug connector as shown in FIG. 1.

Referring to FIG. 1 and FIG. 2, an audio plug connector 100 according to the present invention is shown. The audio plug connector 100 includes a main member 10 of substantially cylindrical shape, with a plurality of contacts 11, 12 13, 14 exposed along an axis direction thereof for transmitting sound signals. The contacts 11, 12, 13, 14 are insulated from each other by insulators 15 which are formed at the main member 10. A subsidiary member 20 is extended outwards from a rear portion of an outer peripheral surface 16 of the main member 10 to show substantially rectangular board shape. The subsidiary member 20 retains a plurality of conductive terminals 30.

Figure 3:
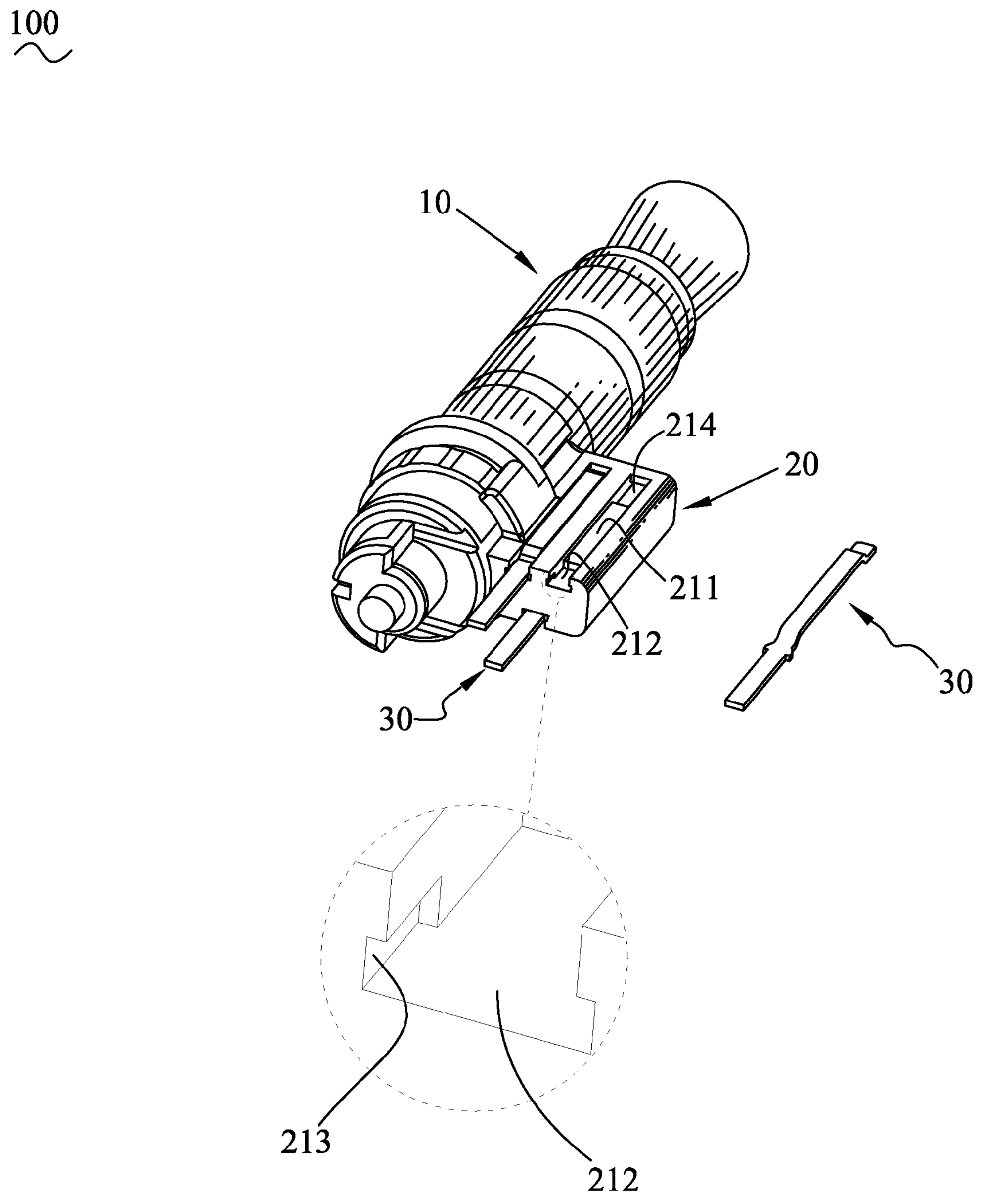
FIG. 3 shows another partially exploded view of the audio plug connector shown in FIG. 1, wherein a portion of a terminal groove is enlarged.

The subsidiary member 20 defines a plurality of terminal grooves 21 for receiving the conductive terminals 30. In this embodiment, the subsidiary member 20 defines three terminal grooves 21 arranged in stagger at two opposing lateral surfaces thereof which are substantially perpendicularly connected to the outer peripheral surface 16 of the main member 10. The terminal groove 21 extends substantially parallel with the axis direction of the main member 10 to penetrate a rear end of the subsidiary member 20 which is finally inserted into a mated audio jack connector (not shown). Each of the terminal grooves 21 includes a front groove 211 and a rear groove 212 deeper than the front groove 211, with a small drop formed therebetween. As best shown in FIG. 3, two opposite sides of the rear groove 212 are respectively recessed opposite to each other to form two limiting recesses 213 communicating with the rear groove 212. A front end of a bottom of the front groove 211 is concaved downwards and passes through a lower portion of a front wall of the terminal groove 21 to form a fixing groove 214, with a stopping portion 215 traversing above the fixing groove 214.

With reference to FIG. 2 again, the audio plug connector 100 includes three independent conductive terminals 30 corresponding to the three terminal grooves 21. Each conductive terminal 30 is of strip shape and has a contacting portion 31, a bent portion 33 bent substantially perpendicular to the contacting portion 31, and a soldering portion 32 extended along an opposite direction of the front contacting portion 31 from a free end of the bent portion 33. The contacting portion 31 has a front portion bent obliquely towards a direction same as an extending direction of the bent portion 33 with respect to the contacting portion 31 to form a buckling portion 34. The soldering portion 32 has two opposite sides protruding laterally to form two wedges 35, adjacent to the bent portion 33.

Referring to FIG. 2 and FIG. 3, in assembly, a fixture may be used to push the conductive terminal 30 along the terminal groove 21 to fix in the terminal groove 21. The contacting portion 31 is received in the front groove 211, the soldering portion 32 is extended beyond the rear groove 212 for being soldered with a PCB (not shown), the buckling portion 34 is embedded in the fixing groove 214 and restrained beneath the stopping portion 215 to become partly invisible, and the wedges 35 are jammed in the limiting recesses 213 for making the conductive terminal 30 securely be fixed in the terminal groove 21.

While the audio plug connector 100 is electrically connected with the mated audio jack connector, because the front end of the contacting portion 31 has the buckling portion 34 inserted into the fixing groove 214 and restrained beneath the stopping portion 215 to be partly invisible, the problem that the contacting portion 31 is tilted out of terminal groove 21 can be avoided during the audio plug connector 100 is inserted in the audio jack connector. Besides, the buckling portion 34 is engaged with the stopping portion 215, and the wedges 35 are jammed in the limiting recesses 213, the relative movement of the conductive terminal 30 in the terminal groove 21 is eliminated. So the conductive terminal 30 can be fixed in the terminal groove 21 securely, even though the audio plug connector 100 is inserted in and drawn out of the audio jack connector frequently. Thus, the disadvantages in the prior art are overcome. The audio plug connector 100 in accordance with the present invention can provide a stable transmission effect with the mated audio jack connector.

As described above, the buckling portion 34 is received into the fixing groove 214 and restrained beneath the stopping portion 215 for preventing the terminal 30 from being tilted outside in insertion and withdrawal. The wedges 35 are jammed in the limiting recesses 213, which ensures the conductive terminal 30 to be fixed in the terminal groove 21 firmly, thereby preventing the conductive terminal 30 relatively sliding in the terminal groove 21.

The foregoing description of the present invention has been presented for purposes of illustration and description. It is not intended to be exhaustive or to limit the invention to the precise form disclosed, and obviously many modifications and variations are possible in light of the above teaching. Such modifications and variations that may be apparent to those skilled in the art are intended to be included within the scope of this invention as defined by the accompanying claims.

What is claimed is:

1. An audio plug connector for mating with an audio jack connector, comprising:

a main member of substantially cylindrical shape with a plurality of contacts exposed along an axis direction thereof;

a subsidiary member extended from a portion of an outer peripheral surface of the main member, the subsidiary member defining at least one terminal groove at a lateral surface thereof, the terminal groove extending substantially parallel with the axis direction of the main member to penetrate a rear end of the subsidiary member which is finally inserted into the audio jack connector, a front end of a bottom of the terminal groove concaved downwards and passing through a lower portion of a front wall of the terminal groove to form a fixing groove, with a stopping portion traversing above the fixing groove; and at least one conductive terminal of strip shape received in the corresponding terminal groove, a rear end of the conductive terminal extending out of a rear end of the terminal groove, a front end of the conductive terminal being bent and extended opposite to the rear end of the conductive terminal to form a buckling portion inserted into the corresponding fixing groove of the subsidiary member, with a free end thereof restrained beneath the stopping portion.

2. The audio plug connector as claimed in claim 1, wherein the terminal groove is defined at one lateral surface substantially perpendicularly connected to the outer peripheral surface.

3. The audio plug connector as claimed in claim 2, wherein the subsidiary member has two parallel lateral surfaces substantially perpendicularly connected to the outer peripheral surface.

4. The audio plug connector as claimed in claim 1, wherein the conductive terminal is divided into a front contacting portion, a rear soldering portion with a small drop from the contacting portion, and a middle bent portion connecting the contacting portion and the soldering portion.

5. The audio plug connector as claimed in claim 4, wherein the terminal groove includes a front groove for receiving the contacting portion, and a rear groove deeper than the front groove, the soldering portion is received in the rear groove and extended rearward beyond the rear groove.

6. The audio plug connector as claimed in claim 5, wherein two opposite sides of the rear groove are respectively recessed oppositely to each other to form two limiting recesses communicating with the rear groove, two opposite sides of the soldering portion protrude laterally to form two wedges corresponding with the limiting recesses.

* * * * *